United States Patent
Snichelotto

(10) Patent No.: US 9,392,940 B2
(45) Date of Patent: Jul. 19, 2016

(54) PORTABLE MEDICAL DEVICE FOR ASSISTANCE TO HEART PATIENTS AND METHOD FOR PROCESSING AND TRANSMITTING DATA THROUGH SAID DEVICE

(71) Applicant: MEDICO SPA, Padua (IT)

(72) Inventor: Eugenio Snichelotto, Padua (IT)

(73) Assignee: MEDICO SPA, Padua (IT)

( * ) Notice: Subject to any disclaimer, the term of this patent is extended or adjusted under 35 U.S.C. 154(b) by 0 days.

(21) Appl. No.: 14/425,609

(22) PCT Filed: Oct. 9, 2013

(86) PCT No.: PCT/IB2013/059226
§ 371 (c)(1),
(2) Date: Mar. 3, 2015

(87) PCT Pub. No.: WO2014/064565
PCT Pub. Date: May 1, 2014

(65) Prior Publication Data
US 2015/0223692 A1    Aug. 13, 2015

(30) Foreign Application Priority Data
Oct. 23, 2012 (IT) .............................. PD2012A0311

(51) Int. Cl.
*A61B 5/01* (2006.01)
*A61B 5/00* (2006.01)
*G06F 19/00* (2011.01)
*A61B 5/0464* (2006.01)
*A61N 1/37* (2006.01)
*A61N 1/372* (2006.01)

(52) U.S. Cl.
CPC .............. *A61B 5/0022* (2013.01); *A61B 5/0464* (2013.01); *A61B 5/746* (2013.01); *A61N 1/371* (2013.01); *A61N 1/37211* (2013.01); *A61N 1/37217* (2013.01); *G06F 19/3406* (2013.01); *A61N 1/37247* (2013.01); *A61N 1/37258* (2013.01); *A61N 1/37282* (2013.01); *G06F 19/3418* (2013.01)

(58) Field of Classification Search
CPC .... A61B 5/0022; A61B 5/746; A61B 5/0464; A61N 1/371; A61N 1/37217; A61N 1/37211; A61N 1/37258; A61N 1/37247; A61N 1/37282; G06F 19/3406; G06F 19/3418
See application file for complete search history.

(56) References Cited

U.S. PATENT DOCUMENTS

| | | |
|---|---|---|
| 8,112,151 B1 | 2/2012 | Cogan |
| 2007/0123955 A1* | 5/2007 | Verhoef ............. A61N 1/37282 607/60 |
| 2010/0225468 A1 | 9/2010 | Sievert |
| 2010/0292556 A1 | 11/2010 | Golden |
| 2012/0166680 A1 | 6/2012 | Masoud |
| 2012/0214140 A1 | 8/2012 | Brynelsen |

* cited by examiner

Primary Examiner — Rex R Holmes
(74) Attorney, Agent, or Firm — Themis Law

(57) ABSTRACT

The invention relates to a portable medical device for assistance to heart patients carrying an implanted pacemaker, which includes at least one electric energy accumulator for power supply, at least one electronic card provided with a first wireless communication unit for the reception of data sent by the pacemaker, and a processing unit suited to process the data received from the pacemaker. The device further includes an external casing suited to be grasped by the patient in order to bring it to the pacemaker's transmission field and provided with at least one light signal for communicating the data processed by the processing unit at least partially to the patient.

13 Claims, 1 Drawing Sheet

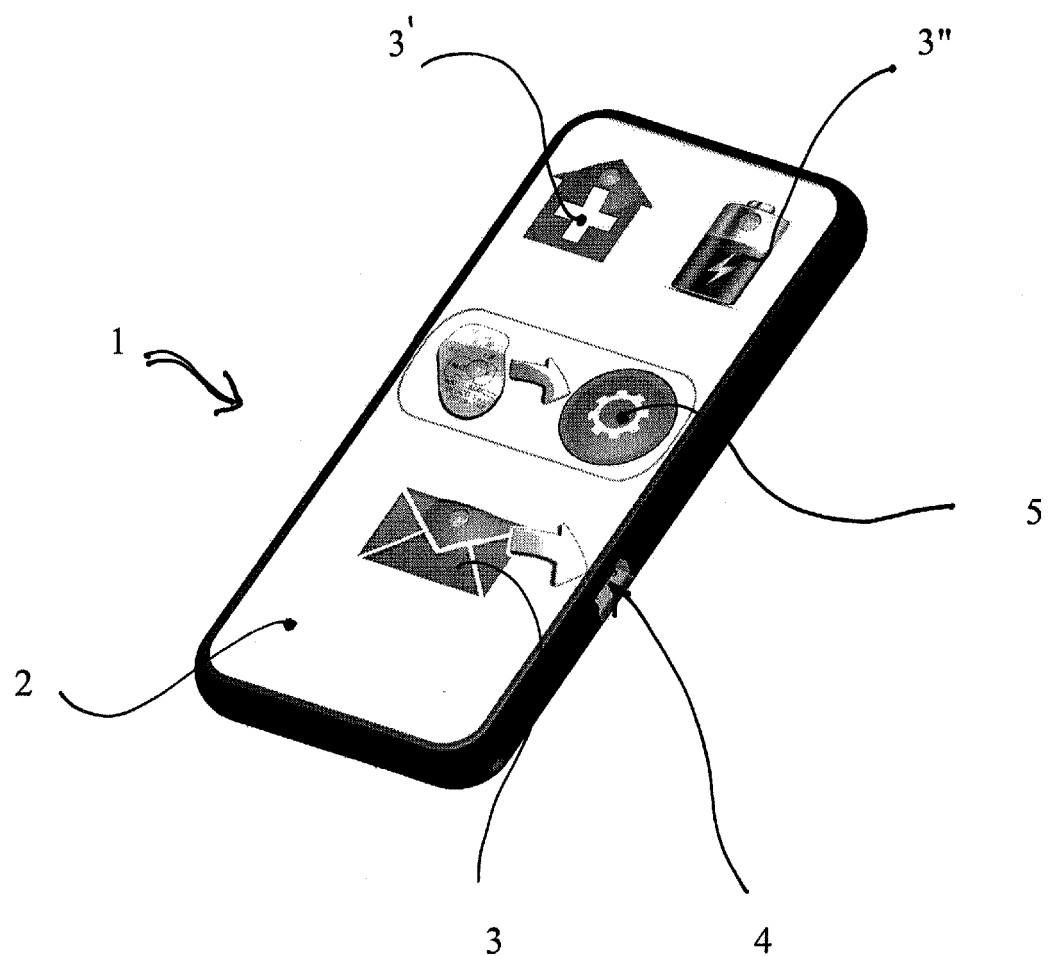

PORTABLE MEDICAL DEVICE FOR ASSISTANCE TO HEART PATIENTS AND METHOD FOR PROCESSING AND TRANSMITTING DATA THROUGH SAID DEVICE

FIELD OF APPLICATION OF THE INVENTION

The present invention can be generally applied in the sector of medical instruments and, in particular, it concerns a portable medical device for assistance to heart patients of the type described in the preamble of claim 1 and a method for processing and transmitting data through a device according to the invention.

STATE OF THE ART

It is known that many patients suffering from heart diseases undergo surgery for the implantation of an electronic stimulation device, called pacemaker, in order to regularize the heart's functions. After implantation, every patient carrying a pacemaker must periodically go to a specialist hospital in order to be visited for a follow-up check of the correct operation of the pacemaker and of the general conditions of the heart muscle. During the check-up, the doctor brings near the patient a device, known per se, for transferring data between the implanted pacemaker and the electronic, check-up apparatus installed in the hospital, so that it is possible to read the data collected, and stored by the pacemaker and if necessary update the operation parameters of the pacemaker itself.

Due to the increasing number of patients carrying an implanted pacemaker, the hospital structures that are responsible for performing the periodical check-ups are often overwhelmed with work, with consequent inconveniences for the patients and non-optimal working conditions for the nursing staff in charge with the performance of the periodical check-ups.

Furthermore, owing to the fact that most of the patients carrying a pacemaker belong to the old age group, the frequent check-ups at the hospital, which can be performed every 5-6 months, can create organizational and logistic problems to the patients.

Furthermore, always due to the relatively old age of the patients, each single visit at the hospital can cause infections and contamination with other diseases. Therefore, a relatively high number of hospital check-ups involves health risks for the patients and increasing organizational problems for the specialist medical structures.

DESCRIPTION OF THE INVENTION

It is a primary object of the present invention to eliminate the drawbacks described above by providing a portable medical device that makes it possible to reduce the number of hospital check-ups for heart patients carrying a pacemaker.

It is a special object of the invention to provide a portable medical device with reduced size and weight, so that the patient can always bring it with himself/herself.

It is a further object of the invention to provide a device that is easy and intuitive to use also for elderly patients.

It is another special object of the invention to provide a device that allows the specialist doctor to frequently monitor heart patients carrying a pacemaker.

These and other objects that will be better described below are achieved by a portable medical device for assistance to heart patients carrying a pacemaker according to claim 1, comprising at least one electric energy accumulator for power supply, at least one electronic card provided with a first wireless communication unit for receiving the data sent by the pacemaker, and a unit for processing the data received from the pacemaker; the device comprises also an external casing suited to be grasped by the patient in order to move it to the pacemaker's transmission field and provided with at least one light signal suited to at least partially communicate to the patient the data processed by the processing unit.

Thanks to this special configuration of the device, the patient can easily monitor the conditions of his/her heart and of the pacemaker with no need to go to a specialist hospital.

Preferably, the electronic card may comprise a second communication unit, of the wired type, with an external electronic processor for the successive transfer of the data received from the pacemaker to the family doctor.

Thanks to this special characteristic of the device, the family doctor can monitor the health conditions of the patient from a remote position, with no need for the patient to undergo a hospital check-up.

BRIEF DESCRIPTION OF THE DRAWINGS

The characteristics of the new portable medical device for assistance to heart patients will be highlighted in greater detail in the following description, with reference to the attached drawing, which is provided by way of non-limiting example.

FIG. 1 shows a perspective view of the device according to the invention.

DETAILED DESCRIPTION OF A PREFERRED EMBODIMENT OF THE INVENTION

The device is described with particular reference to the attached drawing, and the reference numbers to be found in the description and in the claims are used to improve the intelligibility of the invention and do not constitute a limitation to the claimed scope of protection.

The portable medical device for assistance to heart patients according to the invention is indicated as a whole by reference number 1.

The portable medical device according to the invention can be used for heart patients carrying a pacemaker. The latter can be provided with a unit for measuring and storing the data concerning the conditions of the patient's heart and/or of the pacemaker and with a unit for the wireless transfer of the stored data. Generally, a pacemaker is capable of transmitting its data within a transmission field proximal to the pacemaker itself. In particular, the portable medical device 1 comprises at least one electric energy accumulator for power supply, which is not illustrated in the drawing and can be a standard or dedicated battery. The device 1 according to the invention also comprises at least one electronic card that is not illustrated in the drawing and is provided with a first wireless communication unit for receiving the data sent by the pacemaker. Said first wireless communication unit can be based on a telemetry protocol, known per se, which can be of various types. Some non-limiting examples of the above can be the Bluetooth, ZigBee, Wifi communication standards. The electronic card also comprises a unit for processing the data received from the pacemaker.

The device 1 has an external casing 2 suited to be grasped by the patient when he/she needs to move the medical device 1 towards the transmission field proximal to the pacemaker. The reduced size of the external casing 2 and the battery power supply always allow the patient to bring the portable medical device 1 with himself/herself.

The external casing 2 is provided with at least one light signal 3 in order to allow the data processed by the processing unit to be at least partially communicated to the patient.

The electronic card may comprise a second communication unit with an external electronic processor. In this way the patient can download the data received from the pacemaker into the external electronic processor, which can be a personal computer or a tablet or a smartphone or another similar device. Successively, the patient can send the data to the family doctor from the external electronic processor, through a standard information technology communication protocol, for example by e-mail, or through an ftp protocol. The second communication unit can be of the wired type, for example of the Ethernet, USB, FireWire or a similar type. The external casing 2 can be provided with a physical port 4 for connecting the terminal of a communication cable.

In a further example of embodiment of the device according to the invention, the electronic card may comprise a third communication unit operating on a mobile cellular network to directly transmit the data received from the pacemaker to the family doctor, without passing through an external electronic processor. The cellular network can be of the GSM, GPRS, EDGE, UMTS, HSPA type.

As shown in FIG. 1, the external casing 2 may comprise at least one button 5 to selectively start reception of the data sent by the pacemaker. Furthermore, the external casing 2 may comprise a plurality of light signals 3, 3', 3" and one or more sound emitters to ensure communication with the patient. The sound emitter can be a buzzer.

The invention concerns also a method for processing and transmitting data by means of a portable medical device 1 according to the invention. The method can be used to provide assistance to heart patients carrying a pacemaker of the type described above. In particular, the method according to the invention comprises a step a) during which the patient positions the portable medical device 1 in the transmission field proximal to the pacemaker, and a step b) in which the portable medical device starts the selective reception of the data sent by the pacemaker. The patient starts the reception step by pressing the start button 5.

The method comprises also a step c) during which the portable medical device 1 processes the data received from the pacemaker, and a step d) in which the data processed by the processing unit are at least partially communicated to the patient. The at least partial communication of the processed data to the patient can take place through one or more light signals 3, 3', 3".

In greater detail, the positioning step a) and the selective start step b) are carried out manually by the patient, while the processing step c) and the step d) of at least partial communication of the data to the patient are automatically carried out by the portable medical device 1.

The method may properly comprise a further step e) in which the data received from the pacemaker are communicated to the family doctor by means of the second wired communication unit and/or the third communication unit operating on a mobile cellular network.

The processing step c) may comprise the determination of selected functional parameters starting from the data received from the pacemaker and the comparison between said selected functional parameters and threshold values of the same parameters. The threshold values of the functional parameters can be set by the family doctor. The processing step c) may also comprise the generation of one or more alarms that are sent out when at least one of the threshold values of the parameters is exceeded. Furthermore, the step d) of communication to the patient may comprise the coming on of one or more light signals 3, 3', 3" in the presence of one or more alarms.

The method according to the invention may comprise a first preliminary step, to be carried out before steps from a) to e), during which the family doctor sets in the portable medical device 1 a first sequence of dates and/or times for the complete execution of all steps from a) to e), and a second sequence of dates and/or times for the execution of steps from a) to d). In this last case, the step e) of data communication to the family doctor can be carried out automatically by the portable medical device 1 only in the presence of one or more alarms. The first sequence refers to a comprehensive type of monitoring, while the second sequence, which will preferably include closer dates, refers to a quicker type of monitoring that does not involve the transmission of the data to the family doctor if all the functional parameters show normal values.

The method may comprise a second preliminary step during which at least one of the light signals and/or sound emitters is automatically activated on a date and/or at a time contained in the first or in the second sequence. In this way, the portable medical device 1 can inform the patient that it is time to perform steps a) and b), after which the device can automatically perform steps from c) to e) in the case of comprehensive monitoring according to the first sequence, or from c) to d) in the case of quick monitoring according to the second sequence. In the latter case, step e) of data communication to the family doctor can be carried out automatically by the portable medical device 1 only in the presence of one or more alarms.

The patient can start the monitoring procedure at any moment, by simply performing steps a) and b) manually. In this case, the portable medical device 1 can successively perform steps from c) to e) automatically, including the transfer of data to the family doctor.

The first preliminary setting step can be carried out by the family doctor and can comprise storage by the doctor, in the portable medical device 1, of the patient's personal data, the family doctor's data and the reference hospital data, and of the date and/or time of the successive hospital check-up scheduled for the patient. The method may comprise a reminder step f) intended to remind the date and/or time of the successive hospital check-up, wherein said step may include the automatic coming on of at least one of the light signals 3, 3', 3" and/or of the sound emitters on the date and/or time of the successive hospital check-up.

The step e) of communication of the data to the family doctor may comprise the automatic generation of a report file in a standard format. In this way the family doctor will receive a file that can be easily opened on a normal personal computer, for example a pdf or tiff file or any standard file suited to represent text and/or graphic information.

The selected functional parameters that are determined starting from the data received from the pacemaker may comprise, by way of non-limiting example: impedance of the connection catheters between the pacemaker and the patient's heart, and/or onset of self-commutation of the pacemaker's sensing polarity, and/or onset of self-commutation of the pacemaker's pacing polarity, and/or duration of an atrial tachycardia, and/or ventricular frequency in the presence of an atrial tachycardia, and/or duration of a ventricular tachycardia, and/or conditions of the pacemaker's battery, and/or expiry of the recommended time for pacemaker replacement.

The data transmitted by the portable medical device to the family doctor may properly comprise the intracavitary ECG (electrocardiogram) graphs generated by the pacemaker in the presence of arrhythmia phenomena.

The above clearly shows that the device according to the invention achieves the set objects and in particular that it makes it possible to reduce the number of hospital check-ups required for heart patients carrying a pacemaker.

Therefore, with reference to the above the description and the attached drawing, the following claims are expressed.

The invention claimed is:

1. A method of processing and transmitting data by a portable medical device for assistance to heart patients carrying an implanted pacemaker comprising:
   providing the portable medical device, which comprises,
   a unit measuring and storing data regarding functionality of a patient's heart or of the pacemaker,
   a wireless unit configured to transmit the stored data stored within a transmission field proximal to the pacemaker,
   at least one electric energy accumulator for power supply,
   at least one electronic card provided with a first wireless communication unit for receiving the data sent by the pacemaker, and a unit for processing the data received from the pacemaker, and
   an external casing configured to be grasped by the patient in order to bring the external casing to the transmission field proximal to the pacemaker and provided with at least one light signal configured to communicate at least partially the data processed by said processing unit to the patient;
   positioning, by the patient, said portable medical device in the transmission field proximal to the pacemaker;
   selectively starting reception of the data sent by the pacemaker by said portable medical device;
   processing the data received from the pacemaker, carried out by said portable medical device; and
   communicating at least partially to the patient the data processed by said processing unit through said at least one light signal,
   wherein said processing step comprises determining selected functional parameters starting from the data received from the pacemaker, comparing said selected functional parameters with threshold values of the same parameters set by the patient's family doctor, and generating one or more alarms to be activated when at least one of said threshold values is exceeded, said communicating step comprising activating said at least one light signal in presence of one or more of said alarms.

2. The method according to claim 1,
   further comprising a first preliminary setting step during which the patient's family doctor sets in said portable medical device a first sequence of dates or times for complete execution of all the method steps and a second sequence of dates or times for execution of the steps of providing, positioning, selectively starting, processing and communicating at least partially, wherein said step communicating the data to the patient's family doctor is carried out automatically by said portable medical device only in presence of one or more of said alarms.

3. The method according to claim 2, further comprising a second preliminary step during which at least one of said light signals or a sound emitter is automatically activated on a date or at a time contained in said first sequence or in said second sequence, so as to instruct the patient to perform said steps of positioning and selectively starting, while said portable medical device performs automatically said steps of processing, communicating at least partially, and communicating the data, or of processing and communicating at least partially, wherein said step of communicating the data to the patient's family doctor is carried out automatically by said portable medical device only in the presence of one or more of said alarms.

4. The method according to claim 2, wherein said first preliminary setting step comprises storing in said portable medical device, by the patient's family doctor, patient's personal data, doctor's data and data of a reference hospital as well as date or time of the patient's next hospital check-up, said method further comprising the step of reminding the date or the time of the next hospital check-up through automatic activation of at least one of said light signals or a sound emitter.

5. The method according to claim 1, and
   wherein the step of communication the data to the patient's family doctor comprises automatically generating a report file in a standard format.

6. The method according to claim 1, wherein said selected functional parameters determined starting from the data received from the pacemaker comprise impedance of connection catheters between the pacemaker and the patient's heart.

7. The method according to claim 1, wherein said selected functional parameters determined starting from the data received from the pacemaker comprise onset of self-commutation of a sensing polarity of the pacemaker.

8. The method according claim 1, wherein said selected functional parameters determined starting from the data received from the pacemaker comprise onset of self-commutation of a pacing polarity of the pacemaker.

9. The method according to claim 1, wherein said selected functional parameters determined starting from the data received from the pacemaker comprise duration of an atrial tachycardia or ventricular frequency in presence of an atrial tachycardia.

10. The method according claim 1, wherein said selected functional parameters determined starting from the data received from the pacemaker comprise duration of a ventricular tachycardia.

11. The method according to claim 1, wherein said selected functional parameters determined starting from the data received from the pacemaker comprise expiration of a recommended pacemaker replacement time.

12. The method according to claim 1, wherein said positioning step and said selectively starting step are carried out manually by the patient, while said processing step and said step of at least partially communicating to the patient are carried out automatically by said portable medical device.

13. The method according to claim 1, further comprising the step of communicating the data received from the pacemaker to the patient's family doctor through a second communication unit of a wired type or a third communication unit operating through a mobile cellular network.

* * * * *